(12) United States Patent
Noda et al.

(10) Patent No.: US 7,097,657 B2
(45) Date of Patent: Aug. 29, 2006

(54) DUAL IV BAG ARRANGEMENT FOR INTRAVASCULAR TEMPERATURE CONTROL CATHETER COOLING CIRCUIT

(75) Inventors: Wayne Arthur Noda, Mission Viejo, CA (US); Lynn M. Shimada, Orange, CA (US)

(73) Assignee: Alsius Corporation, Irvine, CA (US)

( * ) Notice: Subject to any disclaimer, the term of this patent is extended or adjusted under 35 U.S.C. 154(b) by 433 days.

(21) Appl. No.: 10/368,167

(22) Filed: Feb. 18, 2003

(65) Prior Publication Data

US 2004/0162520 A1   Aug. 19, 2004

(51) Int. Cl.
*A61F 7/00* (2006.01)
(52) U.S. Cl. .......................... 607/105; 607/113; 604/113
(58) Field of Classification Search .................. 607/96, 607/104–106, 113–114; 604/113–114, 131–133, 604/151–154, 291
See application file for complete search history.

(56) References Cited

U.S. PATENT DOCUMENTS

| | | | |
|---|---|---|---|
| 3,247,851 A * | 4/1966 | Seibert | 604/291 |
| 3,504,674 A * | 4/1970 | Swenson et al. | 607/105 |
| 3,927,671 A * | 12/1975 | Chittenden et al. | 604/80 |
| 4,249,923 A * | 2/1981 | Walda | 62/394 |
| 5,445,630 A * | 8/1995 | Richmond | 604/411 |
| 6,146,411 A * | 11/2000 | Noda et al. | 607/105 |
| 6,673,098 B1 * | 1/2004 | Machold et al. | 607/96 |
| 2003/0074038 A1 * | 4/2003 | Gruszecki et al. | 607/104 |

* cited by examiner

Primary Examiner—Lee S. Cohen
(74) Attorney, Agent, or Firm—John L. Rogitz

(57) ABSTRACT

A fluid circuit for circulating coolant in a closed loop between an intravascular catheter and a heat exchange system includes a buffer IV bag in fluid flow series with the catheter between the catheter and a pump that pumps the coolant to the heat exchange system. A conventional IV bag is connected by means of a spike and tube to the buffer bag.

11 Claims, 1 Drawing Sheet

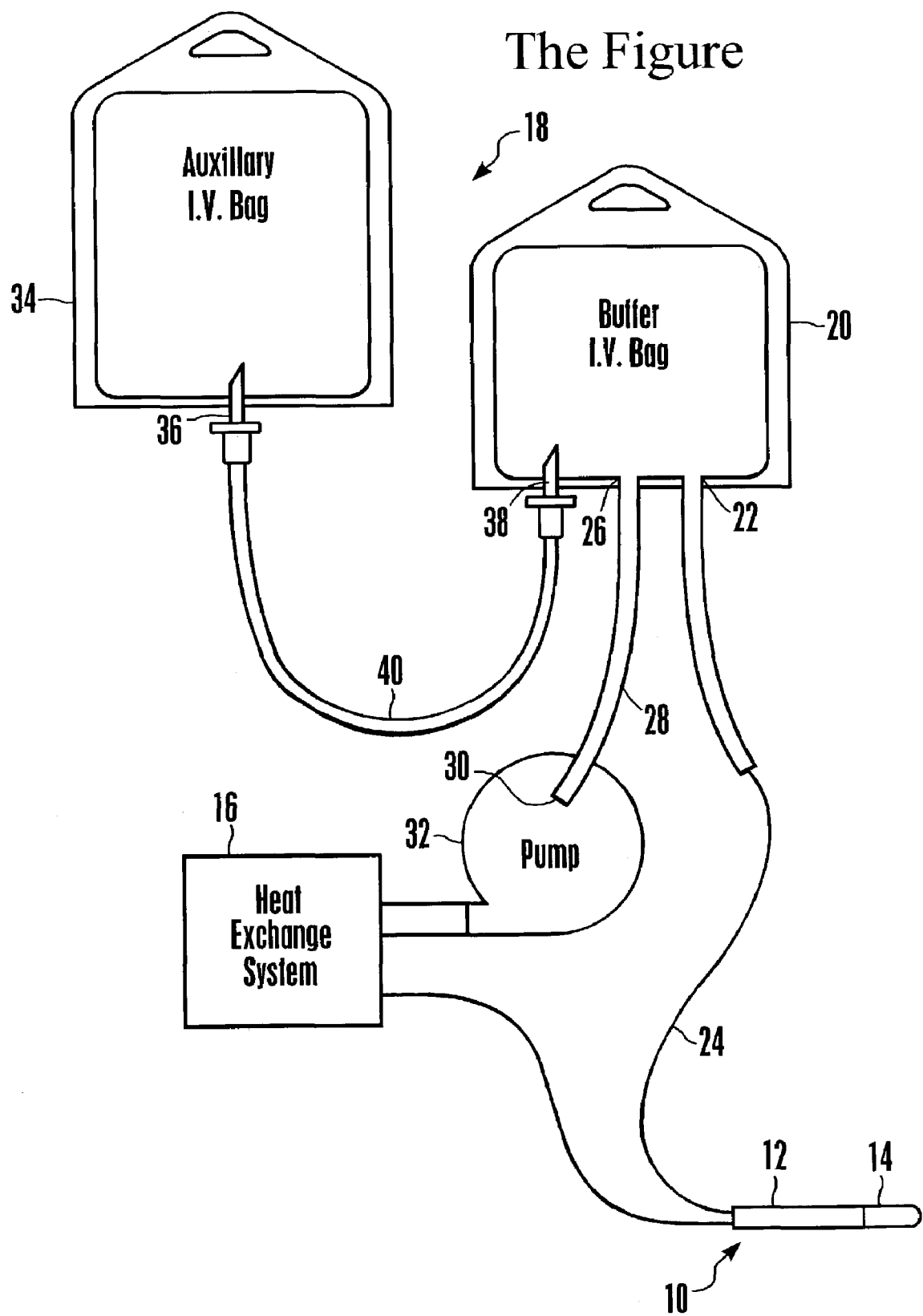
The Figure

DUAL IV BAG ARRANGEMENT FOR INTRAVASCULAR TEMPERATURE CONTROL CATHETER COOLING CIRCUIT

FIELD OF THE INVENTION

The invention relates to intravascular catheters that can be used to control patient temperature.

BACKGROUND OF THE INVENTION

Intravascular catheters have been introduced for controlling patient temperature. Typically, a coolant such as saline is circulated through an intravascular heat exchange catheter, which is positioned in the patient's bloodstream, to cool or heat the blood as appropriate for the patient's condition. The coolant is warmed or cooled by a computer-controlled heat exchanger that is external to the patient and that is in fluid communication with the catheter.

For example, intravascular heat exchange catheters can be used to combat potentially harmful fever in patients suffering from neurological and cardiac conditions such as stroke, subarachnoid hemorrhage, intracerebral hemorrhage, cardiac arrest, and acute myocardial infarction, or to induce therapeutic hypothermia in such patients. Further, such catheters can be used to rewarm patients after, e.g., cardiac surgery or for other reasons. Intravascular catheters afford advantages over external methods of cooling and warming, including more precise temperature control and more convenience on the part of medical personnel.

The following U.S. patents, all of which are incorporated herein by reference, disclose various intravascular catheters/systems/methods: U.S. Pat. Nos. 6,419,643, 6,416,533, 6,409,747, 6,405,080, 6,393,320, 6,368,304, 6,338,727, 6,299,599, 6,290,717, 6,287,326, 6,165,207, 6,149,670, 6,146,411, 6,126,684, 6,306,161, 6,264,679, 6,231,594, 6,149,676, 6,149,673, 6,110,168, 5,989,238, 5,879,329, 5,837,003, 6,383,210, 6,379,378, 6,364,899, 6,325,818, 6,312,452, 6,261,312, 6,254,626, 6,251,130, 6,251,129, 6,245,095, 6,238,428, 6,235,048, 6,231,595, 6,224,624, 6,149,677, 6,096,068, 6,042,559.

SUMMARY OF THE INVENTION

A fluid circuit system for circulating coolant in a closed loop between an intravascular catheter and a heat exchange system includes a buffer IV bag that receives coolant from either the catheter or the heat exchange system and that discharges coolant to the other of the heat exchange system or the catheter. An ancillary IV bag is in fluid communication with the buffer bag.

In a preferred embodiment, coolant flows from the catheter, to the buffer IV bag, and then to a pump, which pumps the coolant to the heat exchange system. The coolant is warmed or cooled as desired and then supplied to the catheter.

The preferred ancillary IV bag is not in fluid flow series with the catheter or the heat exchange system. The ancillary IV bag can be connected to the buffer bag using at least one spike. In contrast, the buffer bag has an inlet receiving coolant and an outlet discharging coolant, with neither the inlet nor outlet requiring a spike connection.

With this combination, the preferred buffer IV bag can be configured and made with materials that allow volumetric compliance to maximize pump performance. Moreover, the buffer IV bag and its tube connections can be configured to be isolated from the ancillary IV bag. This smaller, isolated volume then becomes the amount of saline that would be infused in the instance of a catheter breach, thus minimizing the amount of saline that would be unintentionally infused into the patient if the catheter leaks. Still further, the reduced volume in the buffer IV bag also reduces parasitic heat losses from the system, thereby increasing thermal performance of the system. Also, the buffer IV bag functions as an air trap, facilitating pump priming and ensuring that if the catheter leaks, all the coolant in the bag must first leak into the patient before any air is injected into the patient. This increases system safety. The sizing of the tubing ports minimizes the pressure resistance of the tubing circuit (instead of spikes) under high flow conditions.

In another aspect, a system includes a closed loop heat exchange catheter and a heat exchange system exchanging heat with a coolant circulating between the catheter and the heat exchange system. A buffer bag has an inlet receiving coolant and an outlet discharging coolant. As set forth in greater detail below, the buffer bag is in fluid flow series between the catheter and the heat exchange system.

The details of the present invention, both as to its structure and operation, can best be understood in reference to the accompanying drawings, in which like reference numerals refer to like parts, and in which:

BRIEF DESCRIPTION OF THE DRAWINGS

The FIGURE is a schematic view of the present closed loop catheter system.

DETAILED DESCRIPTION OF THE PREFERRED EMBODIMENT

The FIGURE shows an intravascular heat exchange catheter generally designated 10 that includes a tubular body 12 and a distal segment 14 that establishes a heat exchange element. Coolant such as but not limited to saline is circulated through the catheter 10 in a closed loop to and from a heat exchange system 16 through a fluid circuit, generally designated 18, to heat or cool the coolant as desired to warm or cool a patient. The catheter 10 is made of biocompatible material that may be coated with an anti-coagulant substance such as Heperin®. Preferably, the catheter body 12 is made of flexible plastic, with the heat exchange element 14 being made of inflatable and deflatable medical balloon material, although the present heat exchange element principles apply to, e.g., metal structures as well.

In any case, the catheter 10 is sized to fit within the patient's bloodstream without blocking blood flow and without allowing coolant to enter the bloodstream. The blood can flow around substantially all of the exposed surface areas of the heat exchange elements when the catheter 10 is positioned in the bloodstream and coolant is being circulated through the catheter, to exchange heat with the blood. In a preferred embodiment, the catheter 10 is configured for placement within the venous system, preferably in the superior vena cava or inferior vena cava through the jugular vein or subclavian vein or femoral vein. Less preferably the catheter 10 may be positioned in the arterial system.

Preferred non-limiting uses for the catheter 10 include inducing mild or moderate therapeutic hypothermia in patients suffering a cardiac arrest, acute myocardial infarction, stroke, brain trauma, or undergoing aneurysm surgery. The catheter 10 may also be used to rewarm such patients as well as rewarm patients post-surgery, e.g., post-cardiac bypass surgery.

The fluid circuit 18 includes a buffer IV bag 20 preferably receiving coolant at an inlet 22 from the catheter 10 through a coolant return line 24 through which coolant is discharged from the catheter 10. In the preferred embodiment the buffer IV bag discharges coolant through an outlet 26 to the heat exchange system 16 through an IV line 28. More preferably, fluid flows from the buffer bag 20 to an inlet 30 of a pump 32 that pumps coolant to the heat exchange system 16. The inlet 22 and outlet 26 of the buffer bag 20 are openings that do not require spike-style connections but rather, e.g., Luer-style connections or other high-volume connections to the lines 24, 28 that impede fluid flow less than spike-style connections otherwise would. Thus, the buffer bag 20 is in fluid series flow between the catheter 10 and the heat exchange system 16, and moreover requires no spike to connect it to the circuit, thereby reducing fluid flow resistance relative to a spike connection.

An ancillary IV bag 34, preferably a conventional IV bag, is in fluid communication with the buffer bag 20. As can be appreciated in reference to the FIGURE, the ancillary IV bag 34 is not in fluid flow series with the catheter 10 or the heat exchange system 16. Instead, the ancillary IV bag 34 is connected to the buffer bag 20 using preferably dual-lumen spikes, e.g., an ancillary bag spike 36 engaged with the ancillary bag 34 and a buffer bag spike 38 engaged with the buffer bag 20 and connected to the ancillary bag spike 36 by an IV line 40. Thus, the ancillary IV bag 34 can provide a pressure head on the inlet of the pump 34 as well as a reserve coolant volume for the system through a conventional spike connection without impeding fluid flow through the circuit.

While the particular DUAL IV BAG ARRANGEMENT FOR INTRAVASCULAR TEMPERATURE CONTROL CATHETER COOLING CIRCUIT as herein shown and described in detail is fully capable of attaining the above-described objects of the invention, it is to be understood that it is the presently preferred embodiment of the present invention and is thus representative of the subject matter which is broadly contemplated by the present invention, that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more". All structural and functional equivalents to the elements of the above-described preferred embodiment that are known or later come to be known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. §112, sixth paragraph, unless the element is expressly recited using the phrase "means for" or, in the case of a method claim, the element is recited as a "step" instead of an "act".

What is claimed is:

1. A fluid circuit system for circulating coolant in a closed loop between an intravascular catheter and a heat exchange system, comprising:
   at least one buffer IV bag receiving coolant from one of the catheter, and the heat exchange system and discharging coolant to the other of: the heat exchange system, and the catheter; and
   at least one ancillary IV bag in fluid communication with the buffer bag, wherein the ancillary IV bag is not in fluid flow series with the catheter or the heat exchange system.

2. The system of claim 1, wherein the ancillary IV bag is connected to the buffer bag using at least one spike.

3. The system of claim 1, wherein the buffer bag has an inlet receiving coolant and an outlet discharging coolant.

4. The system of claim 1, wherein the buffer bag is in fluid series flow between the catheter and a pump associated with the heat exchange system.

5. The system of claim 4, wherein fluid flows from the buffer bag to an inlet of the pump.

6. The system of claim 5, wherein fluid flows to the buffer bag from a return line associated with the catheter.

7. A system, comprising:
   at least one closed loop heat exchange catheter;
   at least one heat exchange system exchanging heat with a coolant circulating between the catheter and the heat exchange system;
   at least one buffer bag having an inlet receiving coolant and an outlet discharging coolant, the buffer bag being in fluid flow series between the catheter and the heat exchange system; and
   at least one ancillary IV bag in fluid communication with the buffer bag, the ancillary IV bag not being in fluid flow series with the catheter or the heat exchange system.

8. The system of claim 7, wherein the ancillary IV bag is connected to the buffer bag using at least one spike.

9. The system of claim 7, wherein the buffer bag is in fluid series flow between the catheter and a pump associated with the heat exchange system.

10. The system of claim 9, wherein fluid flows from the buffer bag to an inlet of the pump.

11. The system of claim 10, wherein fluid flows to the buffer bag from a return line associated with the catheter.

* * * * *